(12) United States Patent
O'Rourke et al.

(10) Patent No.: US 6,205,272 B1
(45) Date of Patent: Mar. 20, 2001

(54) FIBER OPTIC PROBE FOR ATTENUATED TOTAL INTERNAL REFLECTION SPECTROPHOTOMETRY

(75) Inventors: Patrick E. O'Rourke, Martinez, GA (US); William R. Toole, Jr., Aiken, SC (US)

(73) Assignee: Equitech Int'l Corp., Aiken, SC (US)

( * ) Notice: Subject to any disclaimer, the term of this patent is extended or adjusted under 35 U.S.C. 154(b) by 0 days.

(21) Appl. No.: 09/032,073

(22) Filed: Feb. 27, 1998

(51) Int. Cl.[7] ..................................................... G02B 6/32
(52) U.S. Cl. .................. 385/33; 385/13; 385/31; 385/36
(58) Field of Search ..................... 385/31, 33, 36, 385/76, 86, 87, 119, 12, 13; 359/534; 250/216, 573, 577

(56) References Cited

U.S. PATENT DOCUMENTS

| | | | |
|---|---|---|---|
| 4,735,477 | * 4/1988 | Bowen | 385/32 |
| 4,986,671 | * 1/1991 | Sun et al. | 374/131 |
| 5,039,224 | 8/1991 | O'Rourke et al. . | |
| 5,142,602 | * 8/1992 | Cabato et al. | 385/87 |
| 5,168,367 | 12/1992 | O'Rourke et al. . | |
| 5,335,067 | 8/1994 | Prather et al. . | |
| 5,348,396 | * 9/1994 | O'Rourke | 374/161 |
| 5,399,876 | * 3/1995 | LaClair | 250/577 |
| 5,402,508 | 3/1995 | O'Rourke . | |
| 5,403,308 | * 4/1995 | Wood et al. | 606/17 |
| 5,407,443 | * 4/1995 | Kobayashi et al. | 606/3 |
| 5,710,626 | * 1/1998 | O'Rourke | 356/301 |
| 5,774,610 | 6/1998 | O'Rourke . | |
| 5,828,797 | * 10/1998 | Minott et al. | 385/12 |

* cited by examiner

Primary Examiner—Hemang Sanghavi
Assistant Examiner—Benjamin Cushwa
(74) Attorney, Agent, or Firm—Maria Reichmanis

(57) ABSTRACT

A fiber optic probe for ATIR (Attenuated Total Internal Reflection) spectrophotometry. The probe includes a housing that contains an optical element or lens, a light-transmitting fiber that directs incident light to the lens, a light-receiving fiber that receives reflected light from the sample interface, a coupler for holding these components in precise alignment, and a flexible armor casing that provides strain relief and protection for the optical fibers. The lens is shaped and dimensioned so that light from the transmitting fiber is reflected at the interface between the lens and the surrounding medium (such as a liquid to be analyzed). The reflected light is transmitted via the transmitting fiber to a suitable spectrophotometer, where the light signal is recorded and analyzed to determine the composition of the sample. The probe is particularly suitable for analyses of fluids and slurries with high optical absorbance.

18 Claims, 3 Drawing Sheets

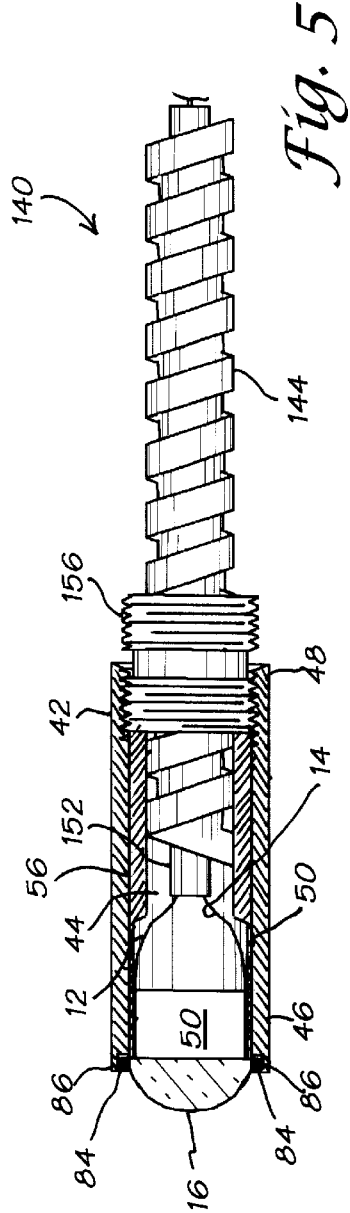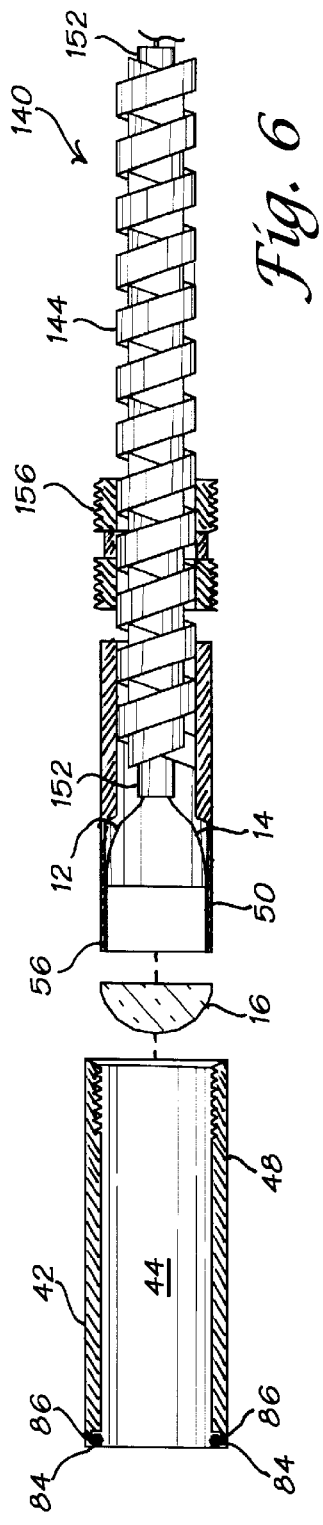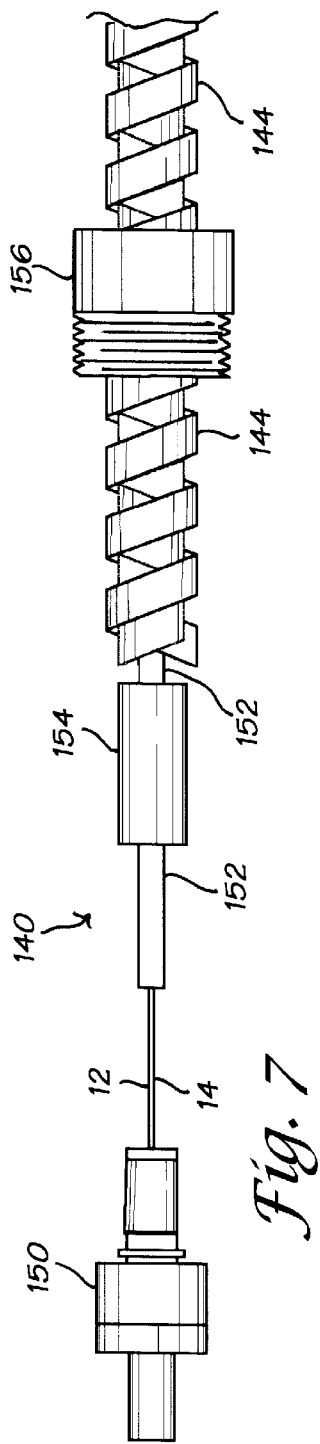

FIBER OPTIC PROBE FOR ATTENUATED TOTAL INTERNAL REFLECTION SPECTROPHOTOMETRY

BACKGROUND OF THE INVENTION

1. Field of the Invention

The present invention relates to fiber optic probes for spectrophotometric analyses. In particular, the present invention relates to a fiber optic probe for attenuated total internal reflection spectroscopy.

2. Discussion of Background

The development of improved optical fibers, multichannel array-type spectrophotometers and multiplexing technology has led to increased use of remote spectroscopic techniques for in-line monitoring and process control, environmental monitoring, and medical applications. Signal transmission via optical fibers allows for the placement of sensitive equipment in central locations, making remote sensing a particularly attractive choice for monitoring processes that take place in harsh industrial process environments. In the environmental field, remote sensing techniques are used for in situ measurements of fluids in wells, boreholes, storage and process tanks, etc. Applications include monitoring groundwater flow, studying the migration of subsurface contaminants, evaluating the progress of remediation operations, and detecting toxic or explosive substances. Fiber optic probes can be used with absorption, diffuse reflectance, and Raman spectroscopy.

Optical analysis techniques also improve the quality of the data. Data obtained from a sample are not always truly representative of the source of that sample, since the mere act of taking the sample can alter its properties; frequently, removing a sample can perturb the source as well. Optical techniques can frequently be implemented without the need to take samples for laboratory analysis elsewhere; therefore, data from optical analyses can be more reliable than data obtained using other analytical techniques.

Absorption or transmission spectrophotometry is perhaps the most versatile and widely used optical analysis technique. The absorbance of a sample is defined as $A=-\log_{10}T$, where $T=I/I_0$, I is the intensity of the light transmitted light transmitted through the sample, and $I_0$ is the incident light intensity. The amount of light absorbed by the sample at different frequencies depends on the concentration of each constituent. Therefore, the absorption spectrum of the sample—the frequency distribution of the absorbance-can be used to identify its composition.

Absorption spectroscopy requires samples that are optically translucent or transparent in the range of frequencies being studied. Therefore, conventional absorption spectroscopy is difficult or impossible for analysis of dark or opaque samples, including inks, dye baths, and other extremely dark fluids. Other techniques based on analysis of the light scattered by the sample, such as diffuse reflectance, fluorescence, total internal reflectance, and Raman spectroscopy, are useful for in situ analysis of dark and opaque liquids, solids or slurries. In probes designed for these types of measurements, light is directed to the sample through a transmitting fiber; scattered or reflected light is collected by the receiving fiber and returned to the detector.

Attenuated total internal reflection spectrophotometry (also known as "ATR" or "ATIR" spectrophotometry) is a useful technique for analyzing dark and opaque liquids and slurries. ATIR is a consequence of internal reflection at the interface between two media having different refractive indices. When light passing through a medium of high refractive index strikes an interface with a medium of low refractive index, total internal reflection occurs if the angle of incidence is greater than the critical angle (wherein the term "critical angle" refers to the angle of incidence above which total internal reflection occurs). That is, the critical angle is that angle r for which $\sin(r)=n_i/n_r$, where $n_i$ and $n_r$ are the refractive indices of the two media with $n_i<n_r$. The attenuation (the decrease in intensity) of the light beam on reflectance is proportional to the change in refractive index between the two media at the interface. Because the refractive index tends to change markedly near absorption bands, the ATIR spectrum of a substance is similar to its absorption spectrum. In general, the ATIR spectrum of a sample is independent of the thickness of the sample, but varies depending on the angle of incidence of the incident light. The smaller the angle of incidence, the greater the penetration into the sample-however, the angle of incidence must be greater than the critical angle for total internal reflection to occur.

A problem that is commonly encountered in ATIR spectrophotometry is the low intensity of the reflected light compared to the intensity of the incident light (the term "attenuated" refers to the common practice of placing an attenuator in the incident beam to balance the energies of the incident and reflected beams). Chemometric techniques may be useful to help factor out background noise and identify the signal of interest.

Like absorption spectrophotometry, ATIR spectrophotometry requires a light source, an optical probe with light-transmitting and light-receiving fibers, and a detector. Suitable probes have a high-index optical element interposed between the fibers and the sample. The element must not only have an index of refraction that is higher than that of samples to be measured, but it must be durable and impervious to the sample constituents. To maximize the light-gathering capacity of the light-receiving fiber, the fibers must be very precisely aligned to optimize the angle of incidence of the light striking the interface between the optical element and the sample. Typical ATIR probes are complex and delicate, and are not well suited for use in many environmental, medical, and industrial process environments. In part because of these problems, ATIR spectrophotometry has been largely confined to research laboratories.

A wide variety of fiber optic probes are available for use with spectrophotometry systems. By way of example, U.S. Pat. No. 5,168,367 describes a variable path length probe for spectrophotometric measurements of fluids in situ. For Raman-type measurements of scattered light, probes designed for improved light coupling efficiency, such as that described in U.S. Pat. No. 5,402,508, are desirable. The probe includes a housing with a transparent window across its tip for protecting the transmitting and receiving fibers. The endfaces of the fibers are slanted, forming a beveled tip that improves light coupling efficiency between the transmitting and receiving fibers. A device for making in situ optical measurements in boreholes, wells, and the like has a support structure bearing one or more probes, each probe disposed at an acute angle (U.S. Pat. No. 5,335,067). A self-referencing probe for in situ optical absorption measurements is shown in U.S. Pat. No. 5,039,224. Additional probe designs are disclosed in the following commonly-assigned, co-pending applications: Ser. No. 08/676,432 (Fiber Optic Probe), filed Jul. 8, 1996; USPS Express Mail Label No. EM 038050777US (Fiber Optic Probe System for Spectrophotometric Analyses), filed herewith; USPS Express Mail Label No. EM 038050735US (Fiber Optic Raman Probe and Coupler Assembly), filed herewith; and USPS Express Mail Label No. EM 038050752US (Retro-Reflecting Probe and Collimating Lens Assembly), filed herewith. The disclosures of the above-referenced patents and patent applications are incorporated herein by reference.

Despite the availability of a variety of fiber optic probes for diverse applications, there is a need for a simple, rugged, inexpensive and easy-to-manufacture probe for ATIR spectrophotometry. Such a probe would further the use of ATIR measurements for on-line monitoring in a wide range of laboratory, medical, environmental, and industrial environments.

SUMMARY OF THE INVENTION

According to its major aspects and broadly stated, the present invention is a probe for ATIR spectrophotometry. The probe includes a housing that contains an optical element or lens, a light-transmitting fiber that directs incident light to the lens, a light-receiving fiber that receives reflected light from the sample interface, a coupler for holding these components in alignment with each other, and, in a preferred embodiment, a flexible armor casing that provides strain relief and shielding for the optical cables. The lens is shaped and dimensioned so that light from the transmitting fiber is reflected at the interface between the lens and the surrounding medium (such as a liquid to be analyzed). The reflected light enters the receiving fiber and is transmitted to a suitable spectrophotometer, where the light signal is recorded and analyzed to determine the composition of the sample. The probe is particularly suitable for analyses of fluids and slurries with high optical absorbance.

An important feature of the present invention is the lens, which is configured to optimize the amount of reflected light that is directed to the receiving fiber. In one preferred embodiment of the invention, the lens is a hemisphere made of a hard, durable, optically transparent and chemically nonreactive material that has a higher index of refraction than the samples to be measured. Suitable materials include, but are not limited to, cubic zirconia, diamond, sapphire, yttrium aluminum garnet, magnesium-aluminum spinel, and quartz. In another preferred embodiment, the lens is a portion of a multifaceted polygon (for example, a dodecagon).

The housing and the coupler constitute another feature of the present invention. The coupler retains the fibers and the lens in optical alignment, so that incident light entering the lens from the transmitting fiber can be reflected back to the receiving fiber. The probe is connected to a suitable light source (preferably, a laser) and a spectrophotometer by optical fibers, thereby facilitating remote monitoring in a wide range of environments. The coupler and the housing, like the lens, are fabricated of materials that are sturdy, durable, and nonreactive in the environment wherein the probe is used.

Still another feature of the present invention is the relative position of the fibers with respect to each other and with respect to the lens. The optimum spacing between the fibers depends on the dimensions of the lens, its index of refraction, and the desired number of internal reflections at the interface. In general, the higher the index of refraction of the lens, the smaller the number of reflections and the higher the intensity of the reflected light signal.

Another feature of the present invention is the flexible armor casing. The casing, which is attached at the proximal end of the probe, allows the fibers to piston, thereby providing strain relief as well as protection from accidental crimping and punctures. The casing may be made of metal or aramid fiber materials such as Kevlar™.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 5 is a partial cross-sectional view of the ATIR probe of FIG. 1, showing the fiber sheath and optional armor casing;

FIG. 6 is a partially-exploded view of the ATIR probe of FIG. 5; and

FIG. 7 is a partially-exploded view of the ATIR probe of FIG. 5, showing the attachment of the armor casing.

DETAILED DESCRIPTION OF A PREFERRED EMBODIMENT

Figure 1:
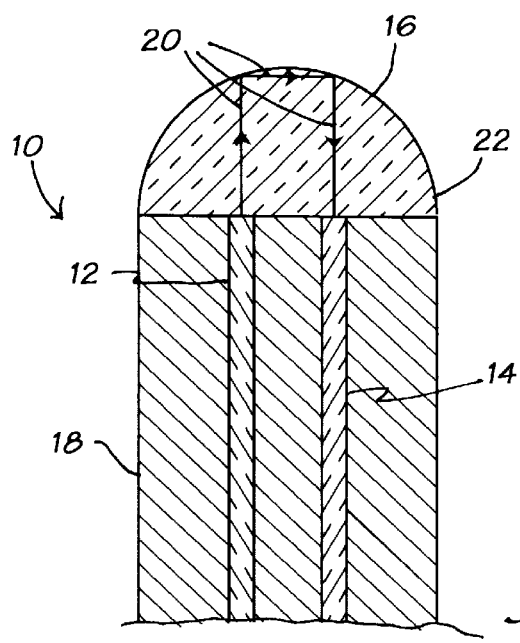
FIG. 1 is a cross-sectional view of the distal end of an ATIR probe with a hemispheric lens tip.

In the following description, reference numerals are used to identify structural elements, portions of elements, or surfaces in the drawings, as such elements, portions or surfaces may be further described or explained by the entire written specification. For consistency, whenever the same numeral is used in different drawings, it indicates the same element, portion, surface and area as when first used. As used herein, the terms "horizontal," "vertical," "left," right," "up," "down," as well as adjectival and adverbial derivatives thereof, refer to the relative orientation of the illustrated structure as the particular drawing figure faces the reader.

An ATIR probe according to a preferred embodiment of the present invention includes an optical element or lens, a light-transmitting fiber that directs incident light to the lens, a light-receiving fiber that receives reflected light from the sample interface, and coupling means for holding these components in precise optical alignment. Such a probe in its simplest embodiment is shown in FIG. 1 (for clarity, only the distal end or probe tip is shown). An ATIR probe 10 includes a first, light-transmitting fiber 12, a second, light-receiving fiber 14, and a hemispheric lens 16. Fibers 12, 14 are spaced apart and fixed in a mount 18, of stainless steel, aluminum, or other suitable material. Mount 18 and lens 16 are preferably fabricated of materials that are sturdy, durable, and nonreactive in the environment wherein probe 10 is used. By way of example, lens 16 may be made of glass, cubic zirconia, sapphire, diamond, spinel, yttrium aluminum garnet, or quartz.

Light from transmitting fiber 12 (indicated by arrows 20) enters lens 16, is reflected at an interface 22 between the lens and the surrounding medium, and enters receiving fiber 14. The reflected light is transmitted via fiber 14 to a suitable detector and spectrophotometer (not shown), where the light signal is recorded and analyzed to determine the composition of the sample. The detected light signal is then analyzed to determine properties such as the spectral profile and intensity.

The optimum spacing between fibers 12, 14 depends on a number of factors, including the dimensions of lens 16, the index of refraction of the lens, and the desired number of reflections at interface 22 that occur before the reflected light reaches fiber 14. When viewed through its flat surface 30, lens 16 exhibits a series of "rings" 32a, 32b, 32c, . . . , each of which represents a polygon traced by light beams that reflect a different number of times inside the lens. That is, a light beam 20 that enters lens 16 from fiber 12 and is reflected twice before reaching fiber 14 describes a square inside the lens, represented by ring 32a; a light beam that is reflected three times describes a hexagon, represented by ring 32b, and so forth. In general, the higher the index of refraction of lens 16, the smaller the critical angle and thus the smaller the minimum number of reflections which can be attained. Thus, the optimum spacing between fibers 12, 14 is best determined by a modest amount of computation and experimentation for each particular application.

Figure 2:
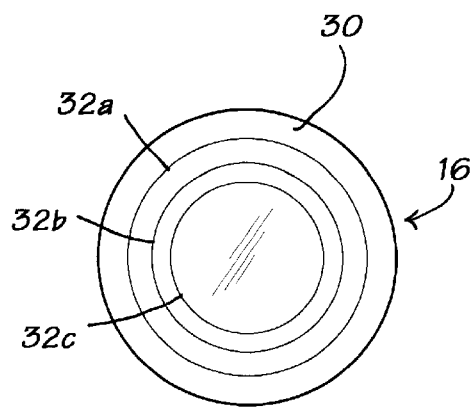
FIG. 2 is a plan view of the bottom of the hemispheric lens of FIG. 1.

Referring now to FIG. 2, there is shown an ATIR probe 40 according to a preferred embodiment of the present invention. Probe 40 includes a probe body or housing 42 with an interior 44, a distal end or tip 46, and a proximal end 48. Probe body 42 is typically cylindrical in shape, and is constructed from stainless steel, aluminum, or some other suitable metal. Preferably, the material of probe body 42 is compatible with the structure of any process vessel where probe 40 will be used, and nonreactive with the environment of use.

Like above-described probe 10, probe 40 has at least one light-transmitting fiber 12, at least one light-receiving fiber 14, and a hemispheric lens 16 positioned in interior 44. Fiber 12 or fiber 14 (or both fibers) may be replaced by fiber bundles if desired. Fibers 12, 14 and lens 16 are maintained in position by a coupler assembly 50. If desired, lens 16 may be protected by a window of sapphire, glass, or other suitable material (not shown).

Suitable in-line devices such as lenses or filters (not shown) may be positioned in optical communication with fibers 12, 14 if desired. In use, transmitting fiber 12 is in optical communication with a suitable light source, receiving fiber 14 is in optical communication with a spectrophotometer.

Coupler 50 may be an SMA-type terminator or some other device that maintains optical fibers or fiber bundles in a fixed position relative to one another. In this case, coupler 50 includes a barrel 52, a bushing 54, and a nut 56 for each of fibers 12, 14. A backing plate 60 and a ring 62 are positioned generally as shown, with O-rings 64, 66, 68 in corresponding recesses 72, 74, 76. A washer 80 (preferably, a spring washer) is interposed between a shoulder 82 of probe body 42 and plate 60; a snap ring 84 is inserted into a recess 86. Fibers 12, 14 may be epoxied into coupler 50. Thus, the components of coupler 50 cooperate to affix the components of probe 40 within probe body 42.

Fibers 12, 14 have a transparent core (such as a fused silica core) enclosed in a cladding having a lower refractive index than the core. If desired, the fibers may be shielded by opaque jackets (not shown). The diameters of fibers 12, 14 are selected to optimize the collection of reflected light by receiving fiber 14, and depend on the dimensions of lens 16. For probes intended for use in a radioactive environment, fibers 12, 14 are selected for good radiation resistance.

A frequently-encountered problem in Raman spectroscopy and other light scattering measurements is the low signal-to-noise ratio, that is, the very low intensity of the Raman-scattered light compared to the intensity of the exciting light. Thus, sensitive detectors with high light gathering power and high stray light rejection are needed to isolate and measure the low intensity Raman signals. Such instruments are costly and delicate, and are not well suited for use in many industrial process environments. Furthermore, monochromatic light transmitted by an optical fiber excites the molecules of optical fibers, causing Raman scattering within the fibers themselves. This "self-scattering" or "silica scattering" generates an additional signal that interferes with the Raman signal collected from the sample.

These problems are particularly evident for small samples and gases. The smaller the sample chamber, the more exciting light is reflected towards the light-receiving fibers by the chamber walls, and the more difficult to detect the Raman signal. The fewer the number of sample molecules, the smaller the Raman signal. Increasing the sample pressure provides more scattering molecules and therefore an increased Raman signal, but does not significantly change the amount of non-Raman-scattered light reaching the detector.

To improve the signal-to-noise ratio, filters may be used to remove a narrow band of wavelengths centered on the wavelength of the laser line. Chemometric techniques are used to factor out background noise and identify the signal of interest. However, the intensity of a typical Raman signal measured with conventional silica-based optical fibers may still be much lower than the intensity of the non-Raman-scattered light reaching the light-receiving fibers. Small samples, such as are desirable in process environments, medical applications, or when dealing with hazardous materials, produce Raman signals that are indistinguishable from background levels even after filtering and data analysis.

For these types of applications, the use of non-silica fibers, such as zirconium fluoride fibers, with relatively low Raman cross-sections has been shown to improve the signal-to-noise ratio over that achievable with silica fibers. Fibers 12, 14 may indeed be any suitable optical fibers for the intended applications of probe 40, including, for example, silica core fiber cables with doped silica cladding having a low OH and a polyimide buffer.

Figure 4:
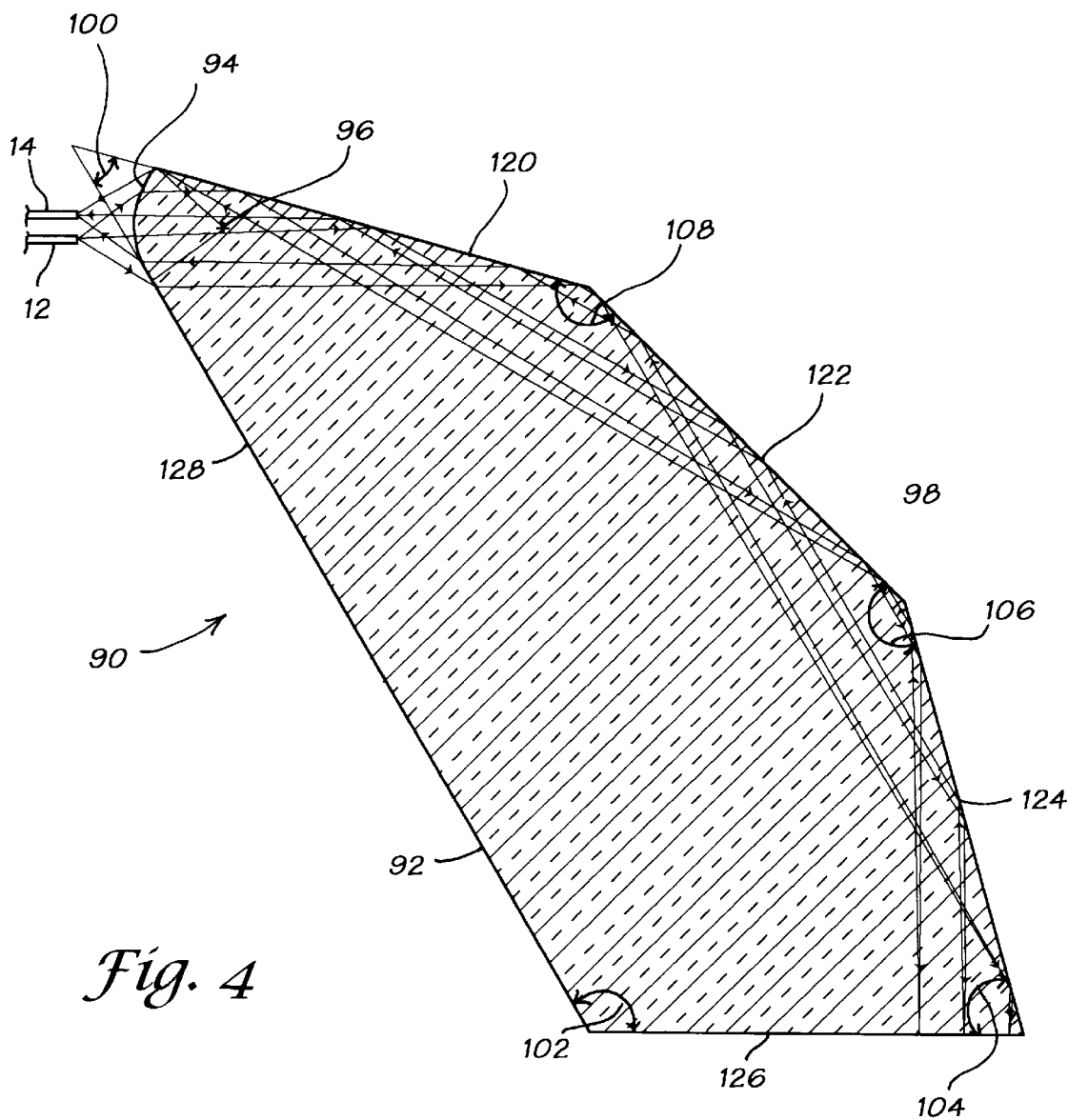
FIG. 4 is a cross-sectional view of the distal end of an ATIR probe according to another preferred embodiment of the present invention.

Another ATIR probe according to the present invention is shown schematically in FIG. 4. A probe 90 has fibers 12, 14 in a suitable fiber mount (not shown) and, instead of lens 16, a prism 92 (for clarity, the probe body, fiber mount, and so forth are not shown). Prism 92 has a spherical entry/exit surface 94 with a center of curvature 96 from which fibers 12, 14 are slightly offset in opposite directions, and a plurality of facets in contact with the liquid to be measured to yield a series of successive internal reflections (indicated by arrows 98). Angles 100, 102, 104, 106, 108 are approximately 30, 120, 75, 150, and 150 degrees, respectively. As will now be evident, prism 92 may be made by cutting a dodecagon into fourths, then shaping one corner to form surface 94.

Light from fiber 12 enters prism 92, is internally reflected at facets 120, 122, 124, then reflected back by a metallized reflecting surface 126. Because fiber 12 is slightly offset from the center of curvature 96, the light does not strike surface 126 precisely perpendicularly, thus, is sent back along a slightly different path and reflects again off facets 124, 122, 120, returning to a slightly different point on surface 94 and thence to fiber 14. Surface 128 may be provided with a light-absorbing coating if desired; alternatively, surface 128 may be left unpolished so that any light reaching the surface is scattered rather than reflected.

The optimum configuration of prism 92 depends on the ratio R between the indices of refraction of the prism and the samples to be measured with probe 90. The larger the angle at which light strikes each facet of prism 92, the larger R must be to obtain total internal reflection. Conversely, with shallow, skimming angles such as are indicated by arrows 98, a smaller P is sufficient. By way of example, if the incidence angle is 75° to normal at each of the three facets of prism 92, a prism made of spinel can be used with any liquid for which the ratio R of refractive indices is 1.035 or higher. In contrast, an octagon-based prism 92 provides an angle of incidence of 67.5°, for a limiting R of 1.082 (corresponding to a maximum sample refractive index of 1.604 at 400 nM). Table I lists the index of refraction of spinel and the maximum index of refraction of a sample liquid for total internal reflection as a function of wavelength:

TABLE I

Refractive index of spinel and maximum refractive index of liquid for occurrence of total internal reflection as a function of wavelength.

| Wavelength (nM) | Spinel | Liquid |
|---|---|---|
| 200 | 1.8748 | 1.811 |
| 300 | 1.7681 | 1.708 |
| 500 | 1.7230 | 1.644 |
| 1000 | 1.7030 | 1,645 |
| 1500 | 1.6954 | 1.638 |
| 2000 | 1.6878 | 1.630 |
| 2500 | 1.6787 | 1.621 |
| 5000 | 1.5980 | 1.544 |

Probes 10, 40, 90 are preferably made of materials that are compatible with any process vessels wherein the probes are to be used, and substantially impervious to the environment in which the probes are used. By way of example, probe body 42 may be of stainless steel; however, brass, aluminum, and alloys such as Inconel™ may also be useful for some applications.

Lenses 16, 92 are made of hard, durable materials that are optically transparent in the frequency range of interest, and have an index of refraction greater than the index of refraction of the samples to be measured. For example, sapphire, quartz, cubic zirconia, spinel, yttrium aluminum garnet ("YAG") and diamond are suitable for use with the invention. Cubic zirconia (popularly known as "CZ") is made from highly purified baddeleyite (a monoclinic form of $ZrO_2$), by adding a small amount of calcium, yttrium, or other impurity. CZ has a high density (5.939) and a high melting point (over 3000° C.). Its Knoop hardness is 1150, higher than that of typical glasses (300–600) or quartz (740) but lower than that of sapphire (2250) or diamond (9000). Its refractive index in the visible and near-infrared ranges from 1.969 (at 405 nM) to 1.868 (at 2325 nM). Yttrium aluminum garnet ($Y_3Al_5O_{12}$) has a density of 4.554, a Knoop hardness of 1350, and a phase change at 2193° C. Diamond has a Knoop hardness of 9000, and changes to graphite at about 1770° C. at ambient pressure.

Generally, materials usable with the invention have a high index of refraction, high heat resistance (high melting point), high Knoop (or MORS) hardness, good flex strength, and good optical transparency in the frequency/wavelength range of interest Table II lists the density, melting point, and index of refraction of some substances that are suitable for use with the present invention.

TABLE II

Properties of substances suitable for prism 92.

| Property | Sapphire | YAG | Cubic Zirconia | Diamond | Spinel |
|---|---|---|---|---|---|
| Maximum temperature (° C.) | 2319 | 2193* | 3110 | 1770* | 2408 |
| Knoop hardness | 2250 | 1350 | 1150 | 9000 | 1650 |
| Flex strength (Mpa) | 1200 | — | 200 | 2940 | 160 |
| Transparency (μM) | 0.19–5.0 | 0.21–5.2 | 0.38–6.0 | 0.24–2.7 | 0.20–5.3 |
| Refractive index (1000 nM) | 1.7557 | 1.8191 | 2.1248 | 2.3929 | 1.7030 |

*phase change

The size of lenses 16, 92 depends in part on the intended application: small lenses 16 with diameters of 1 mm are useful for small samples or in vivo measurements; larger lenses (with diameters of 10–20 mm or more) are useful for environmental measurements or process monitoring. Lens 16 is attached to backing plate 62 by brazing or other suitable technique.

Referring now to FIGS. 5 and 6, there is shown a side, part cross-sectional view of a probe with a flexible armor casing according to the present invention. A probe 140, like above-described probe 40, includes a generally cylindrical probe body 42 with an interior 44, a distal end or tip 46, and a proximal end 48. Probe 140 also includes at least one light-transmitting fiber 12, at least one light-receiving fiber 14, and a hemispheric lens 16 positioned in interior 44. Fiber 12 or fiber 14 (or both fibers) may be replaced by fiber bundles if desired. Fibers 12, 14 and lens 16 are maintained in position by coupler assembly 50 (shown schematically). In-line devices such as lenses or filters (not shown) may be positioned in optical communication with fibers 12, 14 if desired.

Figure 3:
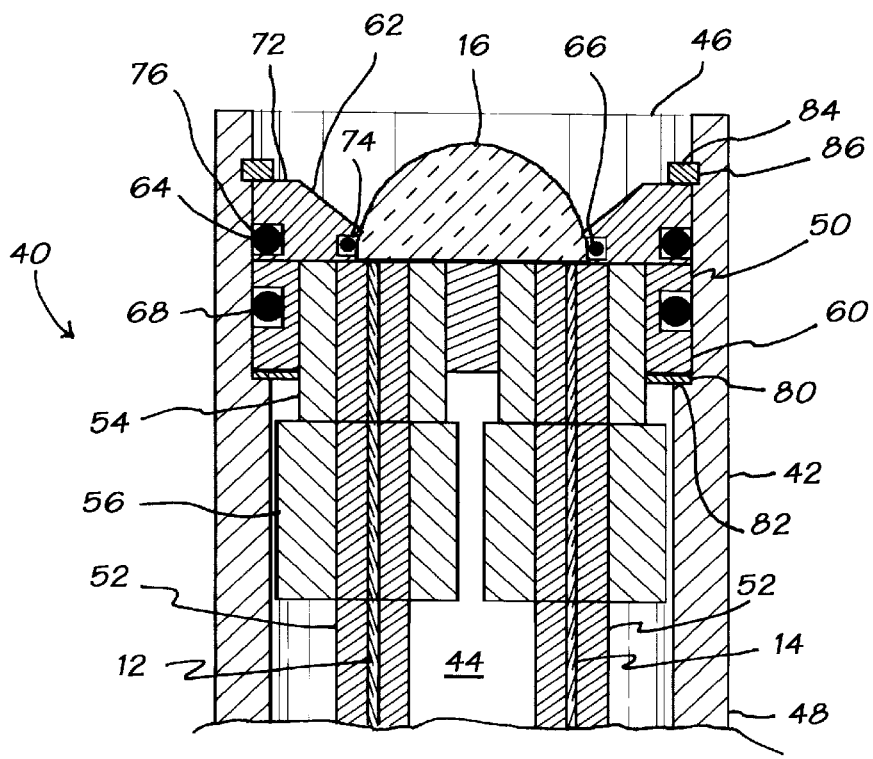
FIG. 3 is a cross-sectional view of the distal end of an ATIR probe according to a preferred embodiment of the present invention.

Coupler 50 may be the type of terminal shown in FIG. 3. Alternatively, lens 16 and coupler 50 are maintained in position by a snap ring or O-ring 84 inserted into a recess 86 (lens 16 may also be affixed to probe body 42 by brazing, cementing, or other suitable technique).

Fibers 12, 14 have a transparent core (such as a fused silica core or a zirconium fluoride core) enclosed in a cladding having a lower refractive index than the core. If desired, the fibers may be shielded by opaque jackets (not shown).

A flexible armor casing 144 is attached at proximal end 48 of probe 140 (FIGS. 5–7). Optical fibers 12, 14 are held in a connector 150 (an SMA terminator or other suitable device), encased in a sheath 152 of Teflon™ or other suitable material, and cemented in place with high-temperature epoxy. Sheath 152 is inserted into a crimp sleeve 154 made of any suitable material, and preferably cemented in place with high-temperature epoxy. Casing 144 is attached to probe body 42 by a back nut 156.

Preferably, casing 144 is attached to one end of fiber sheath 152; the other end of the sheath is loose so that it can piston into and out of casing 58 (i.e., move longitudinally with respect to the casing) to provide strain relief as well as protection. All materials used are selected with a view to the anticipated use of the probe. For example, materials that can withstand high temperatures (on the order of 300° C. or higher), including high-temperature epoxy, Teflon™ tubing, and so forth.

Casing 144 may be made of any suitable metal or alloy; alternatively, casings made of aramid fiber materials such as Kevlar™ may also be useful. Casing 144 not only protects the optical fibers contained therein, but, by reducing mechanical stress on the fibers, it reduces the incidence of breakage. Thus, casing 144 extends the operating lifetime of the probe and reduces maintenance costs.

In use, a probe according to the present invention is placed in contact with the sample to be analyzed (i.e., inserted into a vessel that contains the sample, placed in-line in a process stream, etc.). An input light signal is supplied to transmitting fiber 12 by a laser or other suitable light source, and carried to lens 16 where at least a portion of the signal is reflected to receiving fiber (or fibers) 14. The signal is then directed back to a spectrophotometer for analysis.

A probe according to the present invention is versatile, durable, and economical to manufacture. The probe has an effective path length as small as 0.5 micron, thus, it is especially useful for measurements in inks, dye baths and other extremely dark fluids for which conventional transmission spectroscopy is difficult or impossible.

It will be apparent to those skilled in the art that many changes and substitutions can be made to the preferred embodiment herein described without departing from the spirit and scope of the present invention as defined by the appended claims.

What is claimed is:

1. A fiber optic probe for use in attenuated total internal reflection spectrophotometry, said probe comprising:
    a probe body having an interior;
    at least one light-transmitting fiber in said interior, said transmitting fiber having a distal end;
    at least one light-receiving fiber in said interior, said receiving fiber spaced apart from said transmitting fiber, said receiving fiber having a distal end;
    a hemispherical lens adjacent said distal ends of said transmitting fiber and said receiving fiber, said lens dimensioned and positioned to receive light from said transmitting fiber, internally reflect at least a portion of said light a desired number of times at an interface between said lens and an external medium, and direct at least a portion of said reflected light to said receiving fiber, said transmitting and receiving fibers positioned so that said light is reflected said desired number of times at said interface before entering said receiving fiber, wherein the desired number of reflections is changed by changing the spacing between said light-transmitting fiber and said light-receiving fiber or by changing the composition of said lens; and
    coupling means in said interior for holding said transmitting fiber, said receiving fiber, and said lens in a fixed position with respect to each other within said interior of said housing.

2. The probe as recited in claim 1, wherein said lens is made of a material selected from the group consisting of cubic zirconia, sapphire, diamond, spinel, yttrium aluminum garnet, glass, and quartz.

3. The probe as recited in claim 1, wherein said probe body has a proximal end and a distal end, further comprising a window affixed to said distal end.

4. The probe as recited in claim 1, wherein said transmitting fiber and said receiving fiber are selected from the group consisting of non-silica optical fibers.

5. The probe as recited in claim 1, wherein said transmitting fiber and said receiving fiber are zirconium fluoride fibers.

6. A fiber optic probe for use in attenuated total internal reflection spectrophotometry, said probe comprising:
    a probe body having an interior, a proximal end, and a distal end;
    at least one light-transmitting fiber positioned in said interior, said transmitting fiber having a distal end;
    at least one light-receiving fiber positioned in said interior, said receiving fiber spaced apart from said transmitting fiber, said receiving fiber having a distal end;
    a hemispherical lens having a flat side and a curved side, said flat side adjacent said distal ends of said transmitting fiber and said receiving fiber, said lens dimensioned and positioned so that an optimum portion of light entering said lens from said transmitting fiber is internally reflected a desired number of times at an interface between said lens and an external medium, said transmitting and receiving fibers positioned so that said light is reflected said desired number of times at said interface before entering said receiving fiber, wherein the desired number of reflections is changed by changing the spacing between said light-transmitting fiber and said light-receiving fiber and said light-receiving fiber or by changing the composition of said lens; and
    a coupler fixed in said interior, said coupler holding said transmitting fiber and said receiving fiber in a fixed position with respect to said lens.

7. The probe as recited in claim 6, wherein said lens is made of a material selected from the group consisting of cubic zirconia, sapphire, diamond, spinel, yttrium aluminum garnet, glass, and quartz.

8. The probe as recited in claim 6, wherein said probe body has a proximal end and a distal end, further comprising a window affixed to said distal end.

9. The probe as recited in claim 6, wherein said transmitting fiber and said receiving fiber are selected from the group consisting of non-silica optical fibers.

10. The probe as recited in claim 6, wherein said transmitting fiber and said receiving fiber are zirconium fluoride fibers.

11. The probe as recited in claim 6, wherein said coupler is an SMA-type connector.

12. The probe as recited in claim 6, further comprising a flexible armor casing attached to said proximal end of said probe.

13. A method for making a fiber optic probe for use in attenuated total internal reflection spectrophotometry, said method comprising the steps of:
    fixing at least one light-transmitting fiber in a coupler, said coupler having a longitudinal axis so that said transmitting fiber is approximately parallel to said longitudinal axis;
    fixing at least one light-receiving fiber in said coupler so that said receiving fiber is approximately parallel to said longitudinal axis;
    installing said coupler with said transmitting and receiving fibers in a probe body; and
    installing a lens at a distal end of said probe body, said lens being configured to receive light from said receiving fiber, internally reflect at least a portion of said light a desired number of times at an interface between said lens and an external medium, and direct at least a portion of said reflected light to wherein the desired number of reflections is changed by changing the spacing between said light-transmitting fiber and said light-receiving fiber or by changing the composition of said lens.

14. The method as recited in claim 13, further comprising the steps of:

selecting said lens from a group consisting of generally hemispherical lenses having one flat side and one curved side;

fixing a distal end of said transmitting fiber in optical communication with said flat side; and fixing a distal end of said receiving fiber in optical communication with said flat side.

15. The method as recited in claim 14, wherein said transmitting and receiving fibers each have a proximal end, further comprising the steps of:

placing a connector over said proximal ends so that said proximal ends exit at one end of said connector; and placing a flexible sheath over said proximal ends.

16. The method as recited in claim 14, further comprising the next steps of:

installing a crimp sleeve over said flexible sheath;

installing a flexible armor casing over said crimp sleeve; and affixing said flexible armor casing to said distal end of said probe body.

17. The method as recited in claim 14, wherein said flexible armor casing is made of metal or aramid fiber material.

18. The method as recited in claim 14, further comprising the step of cementing said flexible sheath, said crimp sleeve, and said flexible armor casing with high-temperature epoxy.

* * * * *